US00PP16501P2

(12) United States Plant Patent
Trees

(10) Patent No.: US PP16,501 P2
(45) Date of Patent: May 2, 2006

(54) ***ANGELONIA* PLANT NAMED 'BALANGWITIM'**

(50) Latin Name: *Angelonia angustifolia*
Varietal Denomination: Balangwitim

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 54 days.

(21) Appl. No.: 11/011,313

(22) Filed: Dec. 13, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Angelonia* plant named 'Balangwitim' characterized by its medium-sized white-colored flowers, dark green-colored foliage, and upright mounded growth habit.

1 Drawing Sheet

Latin name of genus and species of plant claimed: *Angelonia angustifolia.*
Variety denomination: 'Balangwitim'.

BACKGROUND OF THE INVENTION

The present invention relates to a new and distinct cultivar of *Angelonia* plant botanically known as *Angelonia angustifolia* and hereinafter referred to by the cultivar name 'Balangwitim'.

The new cultivar was developed by the inventor in a controlled breeding program during February 2002, at Arroyo Grande, Calif. The objective of the breeding program was the development of *Angelonia* cultivars with freely branching and vigorous growth habits, unique flower colors, and continuous flowering.

The female (seed) parent of the new cultivar was the proprietary *Angelonia angustifolia* breeding selection identified as BFP-524, not patented, characterized by its pink-colored flowers and medium green-colored foliage. The male (pollen) parent of the new cultivar was the proprietary *Angelonia angustifolia* breeding selection identified as BFP-642, not patented, characterized by its pink-colored flowers, dark green-colored foliage, and large flowers. The new cultivar was discovered and selected by the inventor as a single flowering plant within the progeny of the above stated cross-pollination during January 2003 in a controlled environment at Arroyo Grande, Calif.

Asexual reproduction of the new cultivar by terminal stem cuttings taken since January 2003 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguished 'Balangwitim' as a new and distinct cultivar of *Angelonia* plant:

1. Medium-sized white-colored flowers.
2. Dark green-colored foliage.
3. Upright mounded growth habit.

Plants of the new cultivar differ from plants of the female parent primarily in flower color and foliage color and from plants of the male parent primarily in flower size and flower color.

'Balangwitim' is similar to the *Angelonia* cultivar Balangloud, U.S. Plant Pat. No. 15,306. However, in side-by-side comparisons, carried out at West Chicago, Ill., plants of the new cultivar differ from plants of 'Balangloud' in the following characteristics:

1. Plants of 'Balangwitim' are shorter than plants of 'Balangloud'.
2. The flowers of 'Balangwitim' are smaller than the flowers of 'Balangloud'.
3. The flowers of 'Balangwitim' have a darker green-colored throat than the flowers of 'Balangloud'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangwitim'. The plants were grown in 10 cm pots for 14 weeks in a greenhouse at West Chicago, Ill.

FIG. 1 illustrates a side view of the overall growth and flowering habit of 'Balangwitim'.

FIG. 2 illustrates a close-up view of an individual flower of 'Balangwitim'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Aug. 9, 2004 at West Chicago, Ill. The readings were taken between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 14 weeks while utilizing a soilless growth medium. Greenhouse temperatures were maintained at approximately 75°–85° F. (24°–29° C.) during the day and approximately 62°–70° F. (17°–21° C.) during the night. Greenhouse light levels were maintained at approximately 6,000 to 10,000 footcandles during the day.

Botanical classification: *Angelonia angustifolia,* cultivar Balangwitim.

Parentage:

*Female (seed) parent.*—Proprietary *Angelonia angustifolia* breeding selection identified as BFP-524, not patented.

*Male (pollen) parent.*—Proprietary *Angelonia angustifolia* breeding selection identified BFP-642, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Crop time.*—Approximately 6 to 7 weeks from a rooted cutting.

*Habit of growth.*—Moderately vigorous with good branching.

*Form.*—Upright mounded.

*Size.*—Height (from soil level to top of plant plane): Approximately 31 cm. Diameter (area of spread): Approximately 59 cm.

*Main branch.*—Quantity per plant: Approximately 4. Shape: Tetrahedral. Strength: Moderate. Length from soil level to base of raceme: Approximately 25 cm. Diameter: Approximately 4 mm. Color: 144B. Texture: Glabrous. Internode length at middle of branch: Approximately 2.8 cm.

*Foliage.*—Quantity: Approximately 10 per branch. Fragrance: None. Type: Simple. Arrangement: Opposite. Orientation to stem: Acute/at right angle. Shape: Lanceolate. Apex: Acute. Base: Sessile. Margin: Serrate. Length of leaf taken from middle of branch: Approximately 5.8 cm. Leaf width: Approximately 1.1 cm. Venation pattern: Pinnate. Color of upper and lower surfaces of young and mature foliage: Slightly lighter than 147A with venation of N144D. Color of lower surface of young and mature foliage: Slightly lighter than 147A with venation of N144D. Texture of upper and lower surfaces: Glabrous.

Flowering description:

*Flowering habit.*—'Balangwitim' is freely flowering under outdoor growing conditions with substantially continuous blooming from spring through autumn and year round in greenhouse environment.

*Lastingness of individual bloom.*—Approximately 7 to 10 days.

*Inflorescence type/description.*—Terminal racemes. Length from base of lowest fully open flower to tip branch: 18 cm. Width: 4 cm. Number per plant: Approximately 6 open racemes per plant. Number of fully open flowers per raceme at any one time: Approximately 15.

Flower description:

*Type/fragrance.*—Solitary, bi-labiate, self-cleaning. Flowers have a slightly sweet fragrance.

*Bud.*—Rate of opening: Generally takes 3–4 days for buds to progress from first color to fully open flowers. Shape: Spherical. Length: Approximately 7.5 mm. Diameter: Approximately 7 mm. Color: Closest to 1D. Texture: Glabrous.

*Flower size/aspect.*—Length: Approximately 1.8 cm. Width: Approximately 1.6 cm. Depth: Approximately 1 cm. Aspect: Facing outward.

*Petals.*—Quantity: Five per flower, fused at base forming a throat, an upper lip having two petals and a lower lip having three petals.

*Upper lip.*—Petal shape: Obovate. Petal apex: Obtuse. Petal margin: Entire. Length of petal: 7 mm. Width of petal: 8 mm. Color of upper surface: Closest to 155B. Color of lower surface: Closest to 155B. Petal texture: Glabrous at margin, densely glandular at base. Gland color: Translucent.

*Lower lip.*—Petal shape: Obovate. Petal apex: Obtuse. Petal margin: Entire. Length of petal: 9.0 mm. Width of petal: 8.0 mm. Color of upper surface of lateral petals: Closest to 155B. Color of lower surface of lateral petals: 155B. Color of upper surface of central petal: Closest to 155B with palate of N144C and teeth of 155C. Color of lower surface of central petal: 155B. Texture of upper surface: Glabrous at margin, densely glandular at base. Gland color: Translucent.

*Throat.*—Length: Approximately 5 mm. Width: Approximately 6 mm. Depth: Approximately 3 mm. Color of inner surface: 155C with 145A at proximal end. Color of outer surface: 155C with 150C at proximal end. Texture of inner surface: Glabrous. Texture of outer surface: Glabrous, pubescent at rim.

*Pedicel.*—Strength: Good. Length: Approximately 1.3 cm. Diameter: Approximately 0.6 mm. Angle to stem: Acute. Color: N144C. Texture: Glabrous.

*Calyx.*—Shape: Cup, formed by 5 sepals fused at base. Length: Approximately 4.0 mm. Width at base: Approximately 1.5 mm. Width at apex: Approximately 3.5 mm. Sepal quantity: 5. Sepal shape: Ovate. Sepal apex: Acuminate. Sepal margin: Entire. Sepal length: Approximately 4 mm. Sepal width: Approximately 1.1 mm. Sepal color: Both surfaces: N144A. Sepal texture: Upper and lower surface: Glabrous.

*Reproductive organs.*—Androecium: Stamen quantity: Four per flower. Stamen length: Approximately 3 mm. Filament color: 155C. Anther length: 1 mm. Anther color: 155C. Amount of pollen: Moderate. Pollen color: 4D. Gynoecium: Pistil quantity: One per flower. Pistil length: 4 mm. Stigma length: 0.5 mm. Stigma color: Colorless and translucent. Style length: 2.5 mm. Style color: 155C. Ovary diameter: 1 mm. Ovary color: N144D.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangwitim', substantially as herein shown and described.

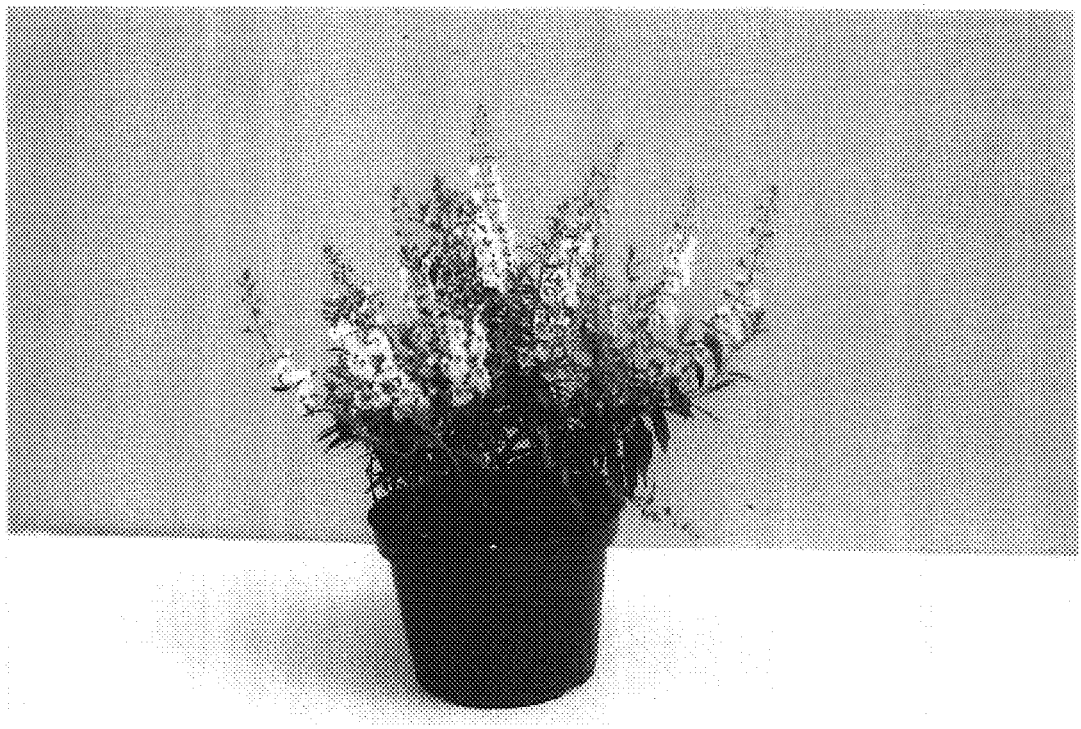
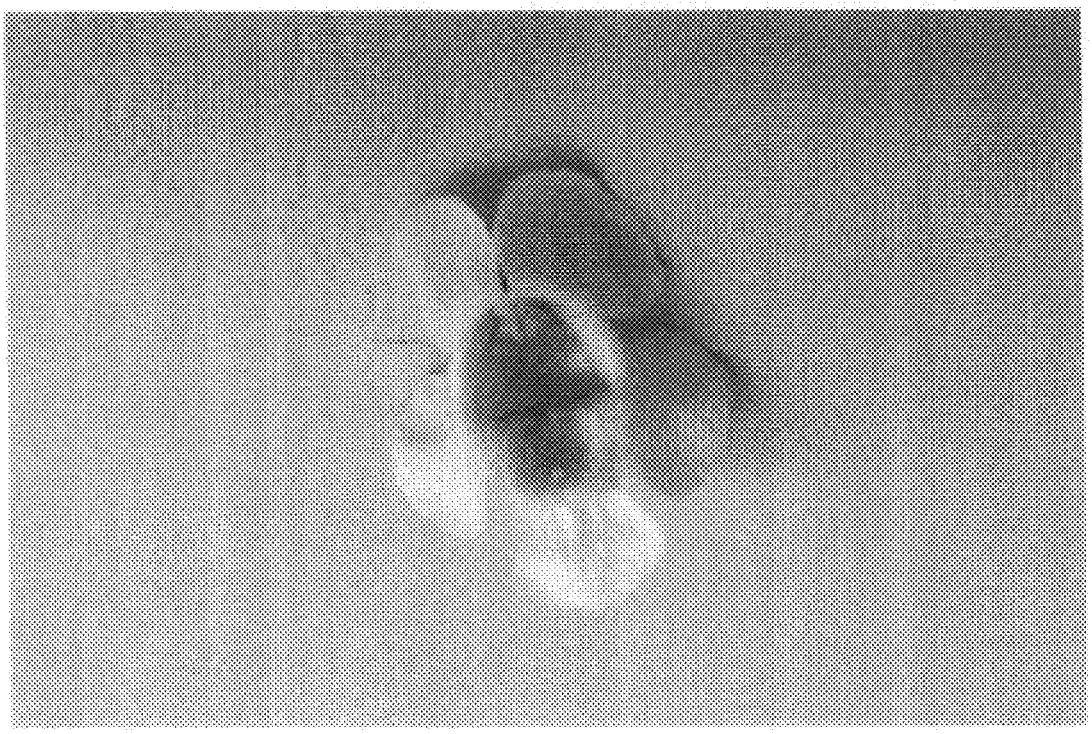

* * * * *